United States Patent [19]
Lee et al.

[11] Patent Number: 5,538,812
[45] Date of Patent: Jul. 23, 1996

[54] ELECTROLYTE MATERIALS CONTAINING HIGHLY DISSOCIATED METAL ION SALTS

[75] Inventors: Hung-Sui Lee, East Setauket; Lin Geng, Coram; Terje A. Skotheim, Shoreham, all of N.Y.

[73] Assignee: Moltech Corporation, Tucson, Ariz.

[21] Appl. No.: 406,293

[22] Filed: Mar. 17, 1995

Related U.S. Application Data

[63] Continuation-in-part of Ser. No. 192,008, Feb. 4, 1994, abandoned.

[51] Int. Cl.$^6$ .................................................. H01M 10/40
[52] U.S. Cl. ........................... 429/192; 429/198; 568/30; 568/35
[58] Field of Search .................... 429/192, 198; 568/28, 30, 35

[56] References Cited

U.S. PATENT DOCUMENTS

| | | | |
|---|---|---|---|
| 2,938,042 | 5/1960 | Stevenson et al. | |
| 3,481,785 | 12/1969 | Ikari | 429/198 |
| 3,689,567 | 9/1972 | Sken et al. | |
| 3,927,100 | 12/1975 | Crovetti et al. | 568/30 |
| 4,068,046 | 1/1978 | Eustace et al. | 429/198 X |
| 4,505,997 | 3/1985 | Armand et al. | 429/192 |
| 4,837,327 | 6/1989 | Stahly | 546/24 |
| 5,162,177 | 10/1992 | Armand et al. | 429/194 |
| 5,350,646 | 9/1994 | Armand et al. | 429/198 X |

*Primary Examiner*—Stephen Kalafut
*Attorney, Agent, or Firm*—Roland Plottel

[57] ABSTRACT

The present invention relates to metal ion salts which can be used in electrolytes for producing electrochemical devices, including both primary and secondary batteries, photoelectrochemical cells and electrochromic displays. The salts have a low energy of dissociation and may be dissolved in a suitable polymer to produce a polymer solid electrolyte or in a polar aprotic liquid solvent to produce a liquid electrolyte. The anion of the salts may be covalently attached to polymer backbones to produce polymer solid electrolytes with exclusive cation conductivity.

20 Claims, 2 Drawing Sheets

ELECTROLYTE MATERIALS CONTAINING HIGHLY DISSOCIATED METAL ION SALTS

This invention was made with government support under Contract No. DE-AC02-76CH00016, between the U.S. Department of Energy and Associated Universities, Inc. The government has certain rights in the invention.

This application is a continuation in part of application Ser. No. 08/192,008, filed Feb. 4, 1994, now abandoned which is incorporated herein by reference.

BACKGROUND OF THE INVENTION

The present invention relates to metal ion salts which can be used in electrolytes for producing electrochemical devices, including both primary and secondary batteries, photoelectrochemical cells and electrochromic displays. The salts have a low energy of dissociation and may be dissolved in a suitable polymer to produce a polymer solid electrolyte or in a polar aprotic liquid solvent to produce a liquid electrolyte. The anion of the salts may be covalently attached to polymer backbones to produce polymer solid electrolytes with exclusive cation conductivity.

The ion conductivity of electrolytes is related to the ability of the anion and the cation to dissociate. A low level of ionic dissociation leads to extensive ion pairing and ion clustering and lower conductivity. This effect is most pronounced in polymer electrolytes, because polymers have lower dielectric constants and lower degree of ion complexation than polar aprotic liquid solvents typically used to produce liquid organic electrolytes.

In addition to facile ionic dissociation, the electrolyte must have a high degree of thermal, chemical and electrochemical stability.

Lithium salts that have been used to produce electrolytes for electrochemical devices have generally been selected from $LiClO_4$, $LiBF_4$, $LiAsF_6$, $LiPF_6$ and $LiSO_2CF_3$. Many of these salts are unstable or produce polymer electrolytes with relatively low conductivity.

U.S. Pat. No. 5,162,177 and U.S. Pat. No. 4,505,997 describe a new class of lithium imide salts of the structure $LiN(SO_2CF_3)_2$. The delocalized anionic charge facilitates dissociation of the ion pair leading to high ionic conductivity both in liquid and polymer solid media. L. A. Dominey in *Extended Abstracts of the Annual Automotive Technology Development Contractors' Coordination Meeting*, Vol. 2, Dearborn, Mich., Nov. 2–5, 1992, describes a methide analogue lithium salt with the composition $LiC(SO_2CF_3)_3$ with similar properties to the imide salts.

None of the above described salts allow covalent attachment to polymer backbones to produce polymeric ion conductors with exclusive cationic conductivity. Exclusive cationic conductivity is advantageous for electrolytes in electrochemical devices, such as batteries, as the deleterious opposing voltages produced by the countermoving anionic charges are thereby eliminated. This leads to higher currents and higher power of the devices. In contrast to the imide and methide salts described above, the lithium salts of the present invention allow covalent attachment to polymer backbones.

SUMMARY OF THE INVENTION

It is apparent that in applications using polymer solid electrolytes, for example, a secondary lithium battery, it would be preferable to have no anion migration. Countermoving anions lead to polarization of the cell and reduced power output. Accordingly, it is a primary object of the present invention to provide a class of lithium salts which allow covalent attachment of the anions to polymer backbones to produce polyelectrolytes with exclusive cation conductivity.

Another object of the invention is to provide a relatively broad class of polymer solid electrolytes, which, when incorporated into a secondary solid state battery, lead to low polarization and high power output.

Still another object is to provide a class of low lattice energy lithium salts which are easily dissociable and are thermally, chemically and electrochemically stable.

These and other objects of the invention are achieved by the synthesis of metal ion salts where the anion is an aromatic moiety with one or more electron withdrawing groups of the formula $SO_2CF_3$ covalently attached. The effect of the electron withdrawing groups is to provide a highly delocalized anionic charge which facilitates the separation of the anion and the cation. Possible methods for covalent attechment of $SO_2CF_3$ groups to aromatic moeties were disclosed by Stevenson et al. in U.S. Pat. No. 2,938,042 and Stahly in U.S. Pat. No. 4,837,327.

The aromatic anions containing an active functional group (vinyl, halogen, amino and others) may be covalently attached to a wide variety of polymer backbones and polymer precursors to produce polyelectrolytes with exclusive cation conductivity. In one preferred embodiment, the polymer backbone consists of a polysiloxane with oligo(ethylene oxide) side chains for complexation of lithium ions which results in salt dissociation.

DETAILED DESCRIPTION OF THE INVENTION

The metal ion salts of the present invention are based on mononuclear or condensed aromatic moieties to which have been covalently attached one or more electron withdrawing groups of the formula $SO_2CF_3$ and one or more hydroxy, amino, or imino groups capable to salt formation and conjugated with $SO_2CF_3$ substituent through aromatic π-electron system. The anionic charge of the such conjugated ionized hydroxy, amino, or imino group is delocalized over the whole π-electronic structure of the aromatic moiety. This delocalization effect is the key to the low lattice energy of the salts and the facile dissociation of the cation from the anion. In particular, the delocalized nature of the anionic charge results in facile dissociation of lithium salts resulting in high ionic conductivity. The chemical structure of several representative examples of the metal ion salts are shown in a structure I–VIII, where M is a metal ion, such as Li, Na, K.

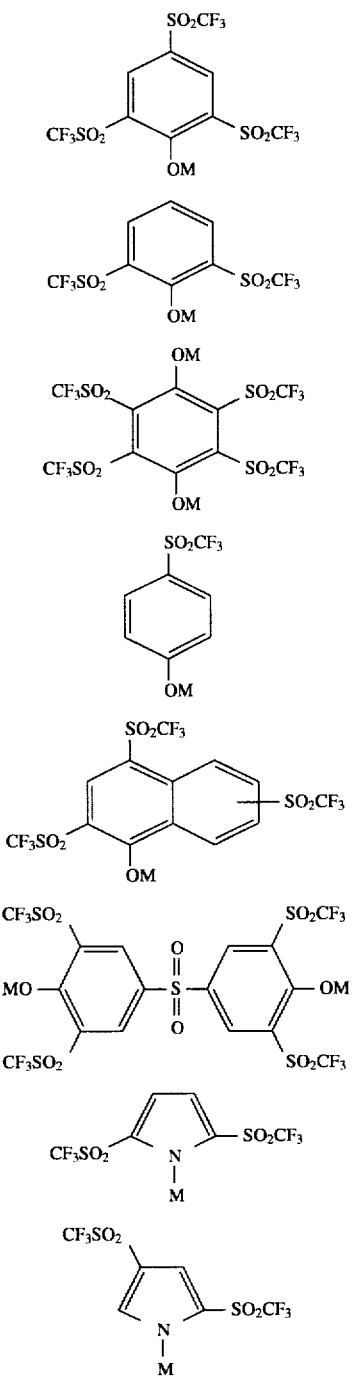

The pyrrole anions are preferably 2,5 and 3,5 substituted pyrroles. The substituted phenols are preferably 2,6 and 2,4,6 substituted phenols. The lithium salts are produced by neutralization with lithium hydroxide. Other lithium compounds, such as lithium-t-butoxide may also be used.

Figure 1:
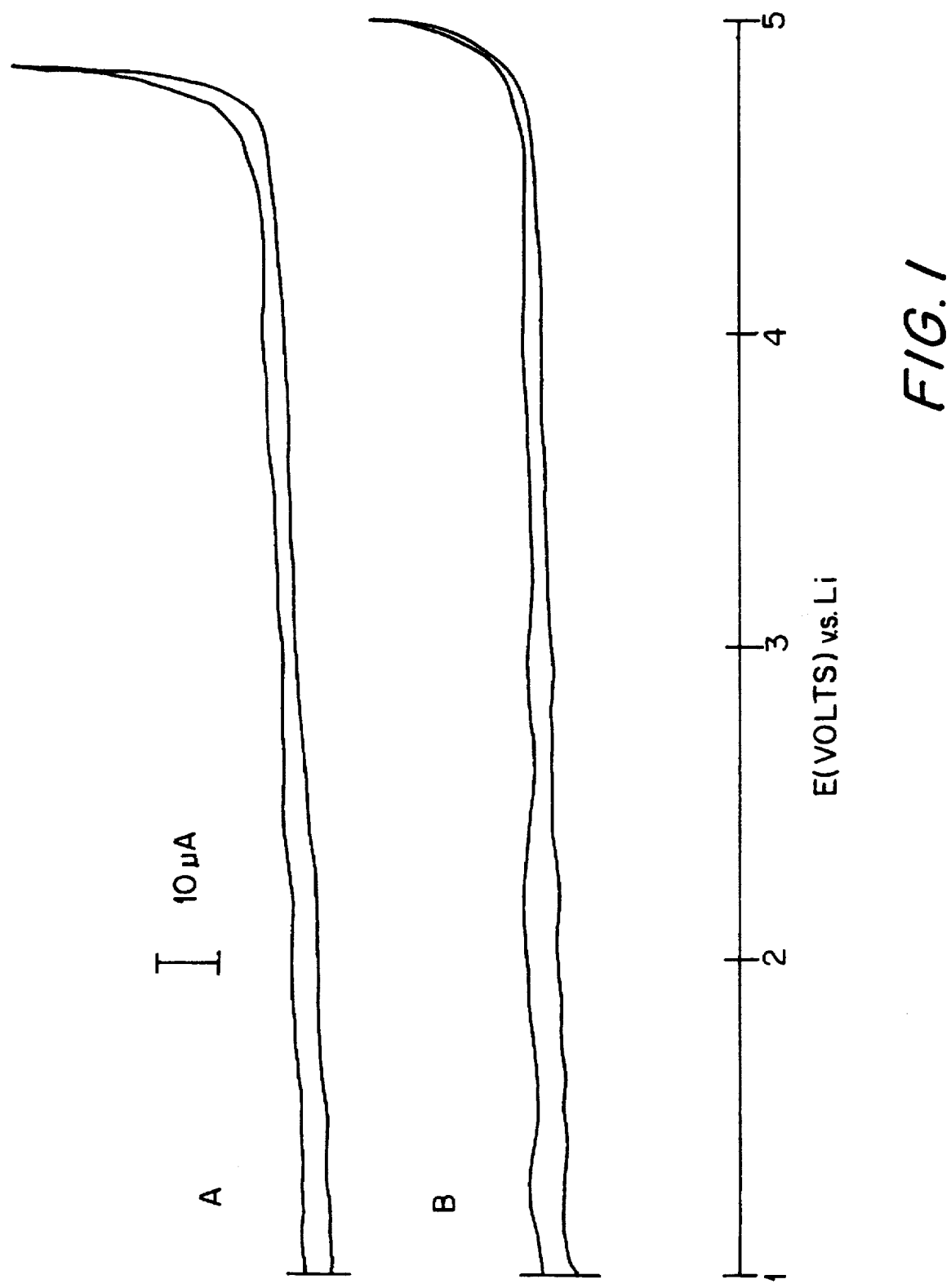
FIG. 1 shows a cyclic voltammogram of $Li[pyrrole(SO_2CF_3)_2]$ (A) and $Li[phenol(SO_2CF_3)_3]$ (B) in propylene carbonate with a glassy carbon working electrode. The scan rate was 50 mV/sec.

The electrochemical stability window of the lithium salts of the present invention was measured in propylene carbonate using cyclic voltammetry. A glassy carbon working electrode and a lithium reference electrode were used. The cyclic voltammogram of Li-bis(trifluoromethylsulfonyl)pyrrole (A) and Li-2,4,6-tris(trifluoromethylsulfonyl)phenol (B) are shown in FIG. 1. The scan rate was 50 mV/sec. The cyclic voltammograms show that the electrochemical stability window is close to 5 volts vs. lithium, which is adequate for secondary lithium battery applications.

In order to produce a high conductivity electrolyte suitable for secondary lithium batteries, the lithium salts may be dissolved in an aprotic polar liquid solvent, selected from propylene or ethylene carbonate, butyrolactone, acetonitrile, benzonitrile, dimethylformamide, diethylformamide, N-methylpyrrolidone, sulfolane, dimethylsulfone, tetramethyl sulfone, diethylether, dimethoxyethane, tetrahydrofuran, dioxane and methyl and ethyl formate.

The conductivities of the lithium salts were measured in THF in order to compare the degree of dissociation. The conductivities of 0.1M THF solutions of various lithium salts are listed in Table 1. The tri-substituted phenolate showed the highest conductivity which is expected due to its extensive anionic charge delocalization. Table 1 shows that the salts of the present invention provides higher conductivities than lithium salts previously studied for secondary lithium batteries, while at the same time allowing covalent attachment to polymer backbones.

TABLE 1

| Conductivities of lithium salts in 1M THF. | |
|---|---|
| Salt | Conductivity (S/cm) at 25° C. |
| $LiCF_3SO_3$ | $2.9 \times 10^{-5}$ |
| $LiN(SO_2CF_3)_2$ | $6.4 \times 10^{-4}$ |
| $LiClO_4$ | $1.7 \times 10^{-4}$ |
| $Li[phenol(SO_2CF_3)]$ | $4.5 \times 10^{-5}$ |
| $Li[phenol(SO_2CF_3)_3]$ | $1.1 \times 10^{-3}$ |
| $Li[pyrrole(SO_2CF_3)_2]$ | $9.4 \times 10^{-4}$ |

Figure 2:
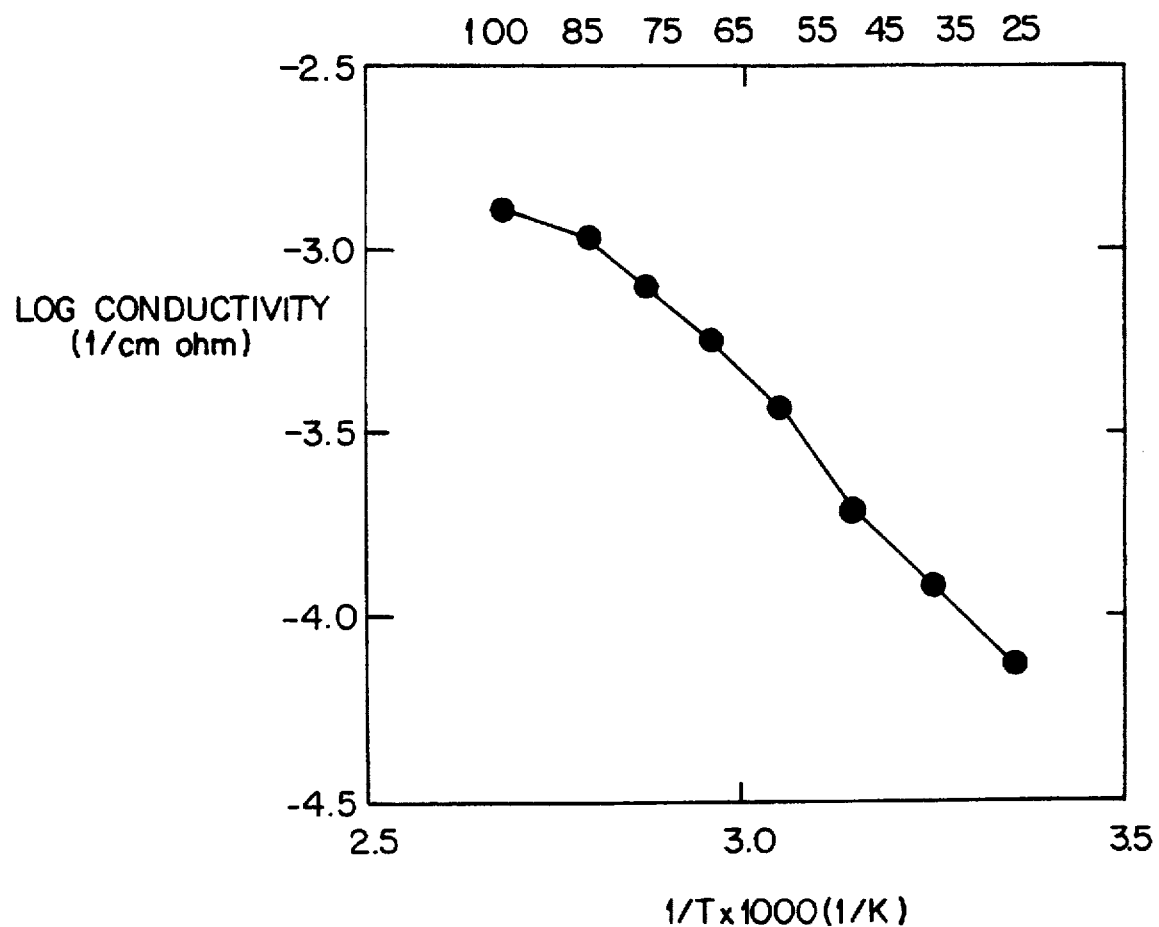
FIG. 2 shows the conductivity as a function of temperature for a polymer electrolyte consisting of $Li[phenol(SO_2CF_3)_3]$ in a branched polysiloxane with oligo(ethylene oxide) side chains.

FIG. 2 shows the conductivity as a function of temperature between 25 ° C. and 100° C. for $Li[phenol(SO_2CF_3)]$ in a branched polysiloxane with oligo(ethylene oxide) side chains. The polymer electrolyte was cast from a THF solution and was dried in vacuum at 60° C. for 24 hours. The ratio of oxygens to lithium was 20:1. The conductivity was measured with ac impedance spectroscopy. The conductivity is almost a factor of ten higher than a corresponding polymer electrolyte with $LiSO_2CF_3$ salt, demonstrating the enhanced charge separation due to anion charge delocalization.

The polyelectrolytes of this invention may be prepared by attaching the anionic moiety, containing an active functional group, directly to the polymer backbone followed by an exchange of the proton in the phenolic OH, the pyrrole NH or the aniline $NH_2$ with lithium. In one alternative, the polyelectrolyte may be prepared by first reacting of such phenol, pyrrole or aniline compound with a polymer precursor, followed by polymerization of the modified precursor and subsequent change of the OH or NH to OLi and NLi.

Polymers with glass transition temperatures in the range from −50° C. to −150° C. are preferred. Low glass transition temperatures allows local segmental motion of the polymer which is necessary for high ionic conductivity. Most preferred are polymers selected from polysiloxanes and polyphosphazenes, which have glass transition temperatures lower than −110° C. Other useful polymer backbones are poly(ethylene oxide) and siloxane-alkylene oxide copolymers. Suitable polymeric systems characterized as having a flexible backbone and a low glass transition temperature are exemplified by the structural formulae IX–X.

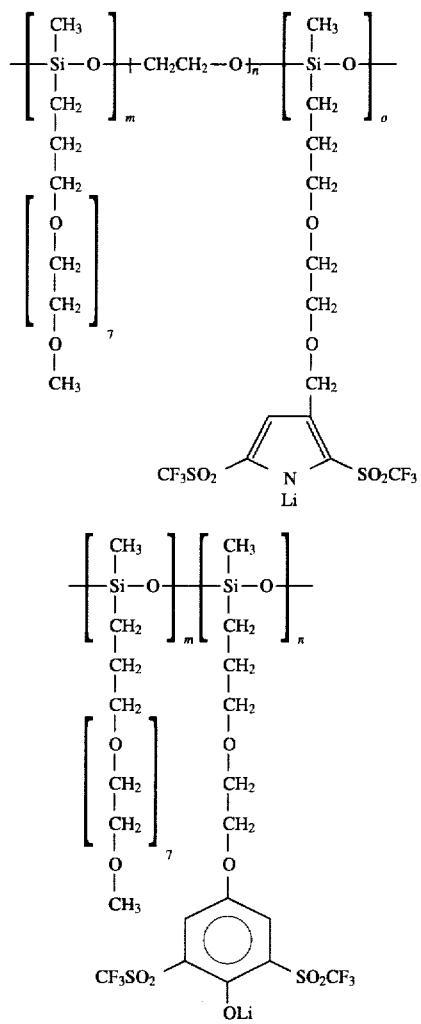

The polymeric systems shown above are intended to be illustrative and are not to be construed as limiting the types of systems contemplated by the present invention.

The manner in which the lithium salts of the present invention are prepared can be understood more fully by reference to the following illustrative examples.

EXAMPLES

Example 1

Preparation of p-trifluoromethylthiophenol (1)

7.33 g of phenol and 6 g of pyridine in 30 ml anhydrous chloroform was cooled with a dry ice bath, followed by addition in portions of 11.7 g of trifluoromethanesulfenyl chloride in 15 ml chloroform. After completion, the yellow solution was stirred at room temperature overnight. The reaction mixture was then washed with water and diluted with hydrochloric acid. After the solvent was evaporated, the residue was distilled under vacuum. The fraction was collected at 66°–67° C./2 mm. The yield was 6 g. NMR: (CDCl$_3$), δ 7.25 (AB pattern of phenyl ring) ppm. IR (neat): 3366.4, 1585.8, 1496.8, 1446.3, 1258.7, 1117.8, 833.9, 755.5 cm$^{-1}$.

Example 2

Preparation of p-trifluoromethylsulfonyl phenol (2)

Compound (1) from Example 1 (3.8 g in 4 ml of glacial acetic acid) was refluxed with 5.4 g of 30% hydrogen peroxide for 7 hours. The solvent was then evaporated and the residue distilled with a Kugelrohr and the boiling point was 140° C./0.1 mm. The solution was then cooled and crystals were formed in the liquid. The melting point if the crystal solid was 108°–110° C. NMR: (CDCl$_3$), δ 7.5 (AB pattern) ppm. IR (KBr): 3440.4, 1587.6, 1501.8, 1441.7, 1347.2, 1295.7, 1192.3, 1116.3, 1058.5, 821.8, 746.7 cm$^{-1}$,.

Example 3

Preparation of lithium p-trifluoromethylsulfonyl phenolate (3)

Compound (2) from Example 2, in anhydrous methanol, was neutralized with equivalent amount of lithium hydroxide: The solvent was then removed, and the residue dissolved in a small amount of anhydrous THF. Ether was subsequently added and the solution stored in a refrigerator. The precipitated crystals were filtered and washed with ether.

Example 4

Preparation of 2,4,6-tris(trifluoromethylthio)phenol (4)

Condensed 32.5 g of trifluoromethylsulphenyl chloride was placed in a pressured bottle in a dry ice bath. 60 ml of chilled chloroform was added under nitrogen, followed by the addition of 5.6 g of phenol in 16 g of pyridine and 0.8 g of iron powder. The mixture was stirred in a closed bottle at room temperature for two days. The solution was then washed with water and diluted with hydrochloric acid. After removal of the solvent, the crude product was distilled with a column. The yield was 10 g. The b.p. was 51° C./0.1 mm. NMR (CDCl$_3$), δ 8.1 (s) ppm.

Example 5

Preparation of 2,4,6-tris(trifluoromethylsulfonyl)phenol (5)

The same oxidation method as in Example 2 was used. The crude solid product was extracted with hot benzene. Needle crystals were obtained with a m.p. of 170°–171° C. The yield was 62%. NMR(CDCl$_3$): δ 8.9(s) ppm. IR (KBr): 3418.1, 1626.5, 1427.6, 1356.8, 1212.2, 1160, 1064.7, 866.6, 782.5 cm$^{-1}$.

Example 6

Preparation of 2,4 and 2,5-bis(trifluoromethylthio)pyrrole (6 and 7, respectively)

Method A: Condensed 24 g of trifluoromethanesulfenyl chloride was placed in a pressured bottle in dry ice, and 2.34 g of pyrrole in 10 ml of anhydrous ether and 1 ml of trifluoromethanesulfonic acid were added. After stirring for 4 hours, the reaction mixture was removed from the dry ice bath and the mixture allowed to react at room temperature for 5 days. The mixture was then washed with water and diluted sodium carbonate. After removal of the ether by vacuum distillation with a column, 2,5-bis(trifluoromethylthio)pyrrole (6) was collected with a b.p. of 58° C./12 mm, and 2,4-bis(trifluoromethylthio)pyrrole (7) with a b.p. of 75° C./12 min. The yields were 21% and 28%, respectively. NMR (CDCl$_3$): compound δ 6.7 (d) ppm. Compound 7: δ 6.9 (s, 1H), 7.3 (s, 1H) ppm. IR (neat): Compound 6: 3468.8, 3138.6, 1609.6, 1522, 1397.4, 1109.7, 1043.5, 936.2, 788.5, 755.7 cm$^{-1}$. Compound 7: 3471.2, 3137, 1609.6, 1532, 1415.3, 1106.9, 950.7, 832.5, 755.9 cm$^{-1}$.

Method B: 25 g of trifluoromethanesulfenyl chloride was condensed in a pressured bottle in dry ice and 2.34 g of pyrrole in 40 ml of anhydrous chloroform, 12.1 g of pyridine and 0.8 g of iron powder were added. The mixture was then stirred at room temperature for 3 days. It was then filtered to remove insoluble materials. The mixture was washed with water, diluted hydrochloric acid and water again. After evaporation of the solvent, the residue was distilled under vacuum, giving 4.2 g of 2,5-bis(trifluoromethylthio)pyrrole and 3.5 g 2,4-bis(trifluoromethylthio)pyrrole. The total yield was 82%.

Example 7

Preparation of
2,4-bis(trifluoromethylsulfonyl)pyrrole (8)

The same procedure as in the synthesis of tris(trifluorosulfonyl)phenol (Example 4) was used. After removal of the solvent, the residue was recrystallized from chloroform to give plate crystals with a m.p. of 124°–126°. NMR (d-acetone): δ 7.75 (s, 1H). IR (KBr): 3296.8, 3134.2, 3048.1, 2963.6, 1528.5, 1445, 1368.6, 1205.9, 1124, 1064.5, 949.4, 852.2, 713.7 cm$^{-1}$.

Example 8

Preparation of
2,5-bis(trifluoromethylsulfonyl)pyrrole (9)

The same procedure as in Example 7 was used. After the reaction was completed, the mixture was stored in a refrigerator overnight. The resulting needle crystals were washed with water. The m.p. was 146°–147° C. NMR (d-acetone): δ 7.3 (s) ppm. IR (KBr): 3278.7, 3138.6, 3050, 2950, 2870, 1517, 1382.7, 1204.3, 1140.2, 1085.9, 937.5, 803.5, 769.1 cm$^{-1}$.

Example 9

Preparation of
2,6-bis(trifluoromethylsulfonyl)-4-(4-bromobutyl)phenol (10)

The same method as for compound (5) was used starting from 4-(4-bromobutyl)phenol (10) instead of phenol. After solvent removal colorless liquid was obtained. NMR (CDCl$_3$): δ 1.4 (m, 4H), 2.8 (t, 2H), 3.5 (t, 2H), 7.2 (s, 1H), 8.1 (s, 2H) ppm.

Example 10

Preparation of
2,6-bis(trifluoromethylsulfonyl)-4-(3-butenyl)phenol (11)

24.6 g of potassium t-butoxide was dissolved in 200 ml of anhydrous THF under nitrogen. The solution was cooled with a dry ice bath to keep the inside temperature at −30° C. 4.9 g of compound (10) in 20 ml of THF was dropped into the solution and the mixture was stirred for 1 hour followed by warming to the room temperature. Then the reaction mixture was poused into ice, acidified with diluted hydrochloric acid and extracted with ether. After washing, drying and the solvent removal 3.5 g of liquid product was collected. MNR (CDCl$_3$): δ 2.8 (m, 2H), 3.5 (t, 2H), 4.7–5.0 (m, 2H), 5.5–6.2 m, 1H), 7.2 (s, 1H), 8.1 (s, 2H) ppm.

Example 11

Preparation of
2,6-bis(trifluoromethylsulfonyl)-4-(3-butenyl)phenolate (12)

4.1 g of compound (11) was dissolved in 20 ml of anhydrous methanol and the solution was neutralized with equivalent amount of lithium hydroxide. The solvent was then removed, and the residue was washed with ether and benzene to give white solid.

Example 12

Preparation of siloxane polymer grafted with phenolate (12) and PEO chains (13)

0.3 g of polymethylhydrosiloxane, 0.63 g of compound (12) and 1.33 g of heptaethyleneglicol allylmethylether were mixed in 20 ml of anhydrous THF. several drops of chloroplatinic acid solution was added and the solution was heated at 60° C. for 24 hours. After the mixture was decolorized, the removal of solvent gave the desired product.

While particular embodiments of the invention have been described, it will be understood, of course, that the invention is not limited thereto, and that many obvious modifications and variations thereof can be made, and that such modifications and variations are intended to fall within the scope of the appended claims.

We claim:

1. A metal ion salt, wherein the anion is comprised of a mononuclear, polynuclear, or condensed aromatic moiety to which have been attached one or more electron withdrawing groups of the formula SO$_2$CF$_3$ and one or more hydroxy, amino, or imino groups capable of forming a salt with a metal ion, wherein said hyroxy, amino, or imino group is conjugated with at least one SO$_2$CF$_3$ substituent on an aromatic ring, or wherein separate said aromatic moieties substituted as described above are bonded together by an —SO$_2$— group.

2. A metal ion salt according to claim 1, wherein the anion comprises an SO$_2$CF$_3$-substituted compound selected from the group consisting of phenol, hydroxybiphenyl, aniline, pyrrole, hydroxynaphthalene, hydroxyanthracene, hydroxyphenanthrene, hydroxyphenanthroline, hydroxyphenazine; or any combination of these bonded together by an —SO$_2$— group.

3. A metal ion salt according to claim 1, wherein the metal ion comprises an alkali or alkaline earth metal, a transition metal or a rare earth metal.

4. A polyelectrolyte containing a flexible polymer backbone and covalently attached anions of a metal ion salt according to claim 1.

5. A polyelectrolyte according to claim 4, wherein the polymer backbone is selected from polysiloxane, polyphosphazene, polyether and co-polymers of polysiloxane and polyethers.

6. An electrochemical cell containing a positive electrode, a negative electrode and a liquid electrolyte, said liquid electrolyte comprising a polar aprotic solvent and a metal ion salt according to claim 1.

7. An electrochemical cell according to claim 6, wherein the polar aprotic solvent is selected from the group consisting of propylene carbonate, ethylene carbonate, butyrolactone, acetonitrile, benzonitrile, dimethylformamide, diethylformamide, N-methylpyrrolidone, sulfolane, dimethylsulfone, diethyl ether, dimethoxyethane, tetrahydrofuran, dioxane, methyl formate, ethyl formate; or mixtures thereof.

8. An electrochemical cell according to claim 6, wherein the metal ion is lithium ion.

9. An electrochemical cell containing a positive electrode, a negative electrode and a polyelectrolyte characterized by having a flexible polymer backbone and covalently attached anions of a metal ion salt according to claim 1.

10. An electrochemical cell according to claim 9, wherein the metal ion is lithium ion.

11. An electrochemical cell according to claim 9, wherein the polyelectrolyte is solvent-free.

12. A polyelectrolyte comprising a flexible polymer backbone and covalently attached anions of a metal ion salt wherein the anion is comprised of a mononuclear, polynuclear, or condensed aromatic moiety to which have been attached one or more electron withdrawing groups of the formula $SO_2CF_3$ and one or more hydroxy, amino, or imino group groups capable of forming a salt with a metal ion, wherein said hydroxy, amino, or imino group is conjugated with at least one $SO_2CF_3$ substituent on an aromatic ring, or wherein separate said aromatic moieties substituted as described above are bonded together by an —$SO_2$— group.

13. A polyelectrolyte according to claim 12, wherein the polymer backbone is selected from polysiloxane, polyphosphazene, polyether and copolymers of polysiloxane and polyethers.

14. A polyelectrolyte according to claim 12, wherein the polymer backbone is a polysiloxane.

15. An electrochemical cell comprising a positive electrode, a negative electrode and a liquid electrolyte, said liquid electrolyte comprising a polar aprotic solvent, and a metal ion salt wherein the anion is comprised of a mononuclear, polynuclear, or condensed aromatic moiety to which have been attached one or more electron withdrawing groups of the formula $SO_2CF_3$ and one or more hydroxy, amino, or imino groups capable of forming a salt with a metal ion, wherein said hydroxy, amino, or imino group is conjugated with at least one $SO_2CF_3$ substituent on an aromatic ring, or wherein separate said aromatic moieties substituted as described above are bonded by an —$SO_2$— group.

16. An electrochemical cell according to claim 15, wherein the polar aprotic solvent is selected from the group consisting of propylene carbonate, ethylene carbonate, butyrolactone, acetonitrile, benzonitrile, dimethylformamide, diethylformamide, N-methylpyrrolidone, sulfolane, dimethylsulfone, diethylether, dimethoxyethane, tetrahydrofuran, dioxane, methyl formate or ethyl formate; or mixtures thereof.

17. An electrochemical cell according to claim 15, wherein the metal ion is a lithium ion.

18. An electrochemical cell comprising a positive electrode, a negative electrode and a polyelectrolyte having a flexible polymer backbone and covalently attached anions of a metal ion salt, wherein the anion is comprised of a mononuclear, polynuclear, or condensed aromatic moiety to which have been attached one or more electron withdrawing groups of the formula $SO_2CF_3$ and one or more hydroxy, amino, or imino group groups capable of forming a salt with a metal ion, wherein said hydroxy, amino, or imino group is conjugated with at least one $SO_2CF_3$ substituent on an aromatic ring, or wherein separate said aromatic moieties substituted as described above are bonded together by an —$SO_2$— group.

19. An electrochemical cell according to claim 18, wherein the metal ion is a lithium ion.

20. An electrochemical cell according to claim 18, wherein the polyelectrolyte is solvent-free.

\* \* \* \* \*